(12) United States Patent
Ferrand et al.

(10) Patent No.: US 11,376,109 B2
(45) Date of Patent: Jul. 5, 2022

(54) FLAT PACKAGE FOR A SURGICAL MESH AND A METHOD OF PACKAGING A SURGICAL MESH IN SAID PACKAGE

(71) Applicant: Sofradim Production, Trévoux (FR)

(72) Inventors: Rebecca Ferrand, Cailloux sur Fontaines (FR); Thomas Vial, Villefranche S/Saone (FR); Barbara Grepinet, Reyrieux (FR)

(73) Assignee: SOFRADIM PRODUCTION, Trevoux (FR)

( * ) Notice: Subject to any disclaimer, the term of this patent is extended or adjusted under 35 U.S.C. 154(b) by 775 days.

(21) Appl. No.: 15/096,360

(22) Filed: Apr. 12, 2016

(65) Prior Publication Data

US 2016/0310253 A1 Oct. 27, 2016

(30) Foreign Application Priority Data

Apr. 23, 2015 (EP) .................................... 15305620

(51) Int. Cl.
*A61F 2/00* (2006.01)
*B65B 55/02* (2006.01)
(Continued)

(52) U.S. Cl.
CPC .............. *A61F 2/0095* (2013.01); *B65B 7/02* (2013.01); *B65B 51/22* (2013.01); *B65B 55/02* (2013.01);
(Continued)

(58) Field of Classification Search
CPC ....... A61F 2/0095; A61B 50/30; B65D 75/30; B65D 75/5855; B65B 55/02; B65B 55/18
See application file for complete search history.

(56) References Cited

U.S. PATENT DOCUMENTS 2,917,878 A 12/1959 Henry et al.
3,403,776 A * 10/1968 Denny .................. B65D 75/30
206/363
(Continued)

FOREIGN PATENT DOCUMENTS

CA 1317836 C 5/1993
WO 8603976 A1 7/1986
(Continued)

OTHER PUBLICATIONS

Advantages of cardboard box packaging, https://www.strategiesonline.net/advantages-of-cardboard-box-packaging/ (Year: 2014).*
(Continued)

*Primary Examiner* — Anna K Kinsaul
*Assistant Examiner* — Daniel Jeremy Leeds
(74) *Attorney, Agent, or Firm* — Weber Rosselli & Cannon LLP

(57) ABSTRACT

The invention concerns a flat package for a non sterile protective pouch (16) receiving a sterile surgical mesh; the package includes:
an external envelope (2) including a front panel (3) and a complementary back panel (4),
the inner face of the front panel (3) and the inner face of the back panel (4) being bonded respectively with a front layer (17) and with a back layer (18) of an internal envelope (15) made of a moisture-impervious material,
the front panel (3) and the back panel (4) being jointed along the contours of the external envelope and, the package having an opening end comprising two tearable portions (8) configured to separate the front panel (3) upon which the front layer (17) of the internal envelope (15) is bonded from the back panel (4) upon which the back layer (18) of the internal envelope (15) is attached.

23 Claims, 5 Drawing Sheets

(51) Int. Cl.
*B65B 7/02* (2006.01)
*B65B 51/22* (2006.01)
*B65B 55/18* (2006.01)
*B65D 75/58* (2006.01)
*B65D 79/02* (2006.01)
*B65D 75/30* (2006.01)

(52) U.S. Cl.
CPC .......... *B65B 55/18* (2013.01); *B65D 75/5855* (2013.01); *B65D 79/02* (2013.01); *A61F 2/0063* (2013.01); *B65D 75/30* (2013.01)

(56) References Cited

U.S. PATENT DOCUMENTS

| | | | |
|---|---|---|---|
| 3,613,879 A | 10/1971 | Kemble | |
| 3,616,898 A * | 11/1971 | Massie | B65D 75/30 116/207 |
| 3,618,756 A * | 11/1971 | Trewella | A61F 15/001 206/440 |
| 3,716,961 A * | 2/1973 | Cope | A61F 15/001 53/434 |
| 3,768,725 A * | 10/1973 | Pilaro | A61L 2/26 206/439 |
| 3,926,309 A * | 12/1975 | Center | A61M 25/002 206/364 |
| 3,954,174 A * | 5/1976 | Kraus | B65D 69/00 206/572 |
| 3,967,729 A * | 7/1976 | Tanner, II | A61F 15/001 206/440 |
| 4,121,714 A * | 10/1978 | Daly | A61L 2/26 116/207 |
| 4,279,344 A | 7/1981 | Holloway, Jr. | |
| 4,296,179 A * | 10/1981 | Wardwell | A61F 15/001 156/701 |
| 4,352,429 A * | 10/1982 | Newman | A61F 15/001 206/439 |
| 4,597,765 A * | 7/1986 | Klatt | A61F 2/26 206/205 |
| 4,603,538 A * | 8/1986 | Shave | A61B 17/06133 53/425 |
| 4,630,729 A * | 12/1986 | Hirt | B65D 75/30 156/291 |
| 4,781,297 A * | 11/1988 | Abrahamsson | A61L 2/26 206/439 |
| 5,219,077 A | 6/1993 | Transue | |
| 5,220,769 A * | 6/1993 | Brown | A61B 17/06133 156/289 |
| 5,249,682 A | 10/1993 | Transue | |
| 5,341,922 A * | 8/1994 | Cerwin | A61B 17/06133 206/484.2 |
| 5,972,008 A | 10/1999 | Kalinski et al. | |
| 6,059,112 A | 5/2000 | Dykstra et al. | |
| 6,568,533 B1 * | 5/2003 | Tanaka | B65D 75/30 206/484 |
| 6,685,714 B2 | 2/2004 | Rousseau | |
| 6,889,839 B1 * | 5/2005 | Rosten | B65D 81/075 206/363 |
| 6,976,584 B2 | 12/2005 | Maiola et al. | |
| 7,243,791 B2 | 7/2007 | Detruit et al. | |
| 7,475,776 B2 | 1/2009 | Detruit et al. | |
| 7,481,314 B2 | 1/2009 | Komarnycky | |
| 8,033,395 B2 | 10/2011 | Iwao et al. | |
| 8,142,515 B2 | 3/2012 | Therin et al. | |
| 8,273,436 B2 * | 9/2012 | Flynn | B32B 7/12 40/638 |
| 9,035,121 B1 * | 5/2015 | Goodsell | B65F 1/002 588/249.5 |
| 2004/0000499 A1 | 1/2004 | Maiola et al. | |
| 2004/0068159 A1 | 4/2004 | Neisz et al. | |
| 2004/0238380 A1 * | 12/2004 | Newman | A45C 11/005 206/5.1 |
| 2005/0077197 A1 | 4/2005 | Detruit et al. | |
| 2005/0126948 A1 | 6/2005 | Maiola et al. | |
| 2005/0241981 A1 | 11/2005 | Gupta et al. | |
| 2006/0196788 A1 * | 9/2006 | Komarnycky | A61F 2/0045 206/287 |
| 2007/0084144 A1 * | 4/2007 | Labrecque | A61L 2/07 53/425 |
| 2007/0160408 A1 * | 7/2007 | Peterson | B65D 75/30 400/621 |
| 2007/0170080 A1 * | 7/2007 | Stopek | A61B 17/06114 206/438 |
| 2007/0209957 A1 | 9/2007 | Glenn et al. | |
| 2009/0166236 A1 | 7/2009 | Iwao et al. | |
| 2009/0200198 A1 * | 8/2009 | Guelzow | A61F 2/0095 206/570 |
| 2009/0209031 A1 | 8/2009 | Stopek | |
| 2009/0236253 A1 * | 9/2009 | Merckle | A61L 2/206 206/439 |
| 2009/0314676 A1 * | 12/2009 | Peck | A61L 2/206 206/438 |
| 2010/0005941 A1 * | 1/2010 | Schueppstuhl | B26D 3/085 83/879 |
| 2010/0158991 A1 | 6/2010 | Okada et al. | |
| 2010/0181371 A1 * | 7/2010 | Messmer | B65D 5/4233 229/102 |
| 2010/0288770 A1 | 11/2010 | Marco et al. | |
| 2011/0127188 A1 * | 6/2011 | Thompson | B32B 27/08 206/438 |
| 2011/0139650 A1 * | 6/2011 | Dworak | A61L 2/26 206/363 |
| 2011/0226762 A1 * | 9/2011 | Mermet | A61L 2/26 220/6 |
| 2011/0309073 A1 * | 12/2011 | Dacey | A61F 2/0095 220/6 |
| 2012/0057810 A1 * | 3/2012 | De Klerk | A61L 2/26 383/41 |
| 2012/0187002 A1 | 7/2012 | Wu | |
| 2014/0069461 A1 * | 3/2014 | Gomez | A61K 8/0208 134/6 |
| 2014/0090999 A1 * | 4/2014 | Kirsch | A61B 17/0057 206/438 |
| 2015/0004076 A1 * | 1/2015 | Weisshaupt | A61L 2/26 422/292 |
| 2015/0016756 A1 * | 1/2015 | Down | B65D 75/5833 383/203 |
| 2015/0209129 A1 * | 7/2015 | Bailly | A61F 2/0063 606/151 |
| 2016/0310254 A1 * | 10/2016 | Ferrand | B65D 11/14 |
| 2017/0166367 A1 * | 6/2017 | Minnette | B65D 51/20 |

FOREIGN PATENT DOCUMENTS

| | | |
|---|---|---|
| WO | WO 86/03976 A1 | 7/1986 |
| WO | 2006100372 A1 | 9/2006 |
| WO | 2011128903 A2 | 10/2011 |

OTHER PUBLICATIONS

European Search Report for EP 15305620.5 date of completion is Sep. 25, 2015 (7 pages).

Examination report No. 1 for standard patent application issued in Australian Patent Application No. 2016201920 dated May 20, 2020, 5 pages.

* cited by examiner

FLAT PACKAGE FOR A SURGICAL MESH AND A METHOD OF PACKAGING A SURGICAL MESH IN SAID PACKAGE

CROSS-REFERENCE TO RELATED APPLICATIONS

This application claims benefit of and priority to European Patent Application Serial No. 15305620.5 filed Apr. 23, 2015, the disclosure of the above-identified application is hereby incorporated by reference in its entirety.

TECHNICAL FIELD

The present invention relates to a packaging for a surgical mesh and a method of packaging a surgical mesh in said package.

BACKGROUND OF THE RELATED ART

Wall reinforcement prostheses, for example for the abdominal wall, are widely used in surgery. These prostheses are intended to treat hernias by temporarily or permanently filling a tissue defect. These prostheses are generally made from a surgical mesh, such as a biocompatible prosthetic textile, and can have a number of shapes, for example rectangular, circular or oval, depending on the anatomical structure to which they are to adapt. A surgical mesh is generally flat and may vary in dimensions, from for example 5×10 cm up to 30×50 cm, depending on the size of the defect to be treated.

Before being packaged as a commercial product and shipped to hospitals or end-users, surgical meshes have to be sterilized in order to avoid contamination to the patient whom it is intended to be implanted. Gas sterilization is commonly used in the medical field and surgical meshes are usually sterilized by means of ethylene oxide (EtO) gas. The sterilization process generally requires the immersion of the surgical mesh in ethylene oxide for a time sufficient for the gas to sterilize the surgical mesh. In addition, in order to proceed to ethylene oxide sterilization, the surgical mesh must be previously humidified. Moreover, for handling purposes, the surgical mesh is usually inserted into a handling pouch before being submitted to the sterilization process. The handling pouch is preferably made at least partly of a material which is impervious to contamination by microorganisms, bacteria and/or a biologically active substance which may come into contact with the pouch while it is being handled, while at the same time remaining permeable to a sterilization gas such as for example ethylene oxide. Such a material is for example a nonwoven made of filaments of a high density polyethylene bound together by heat and pressure, such as the product sold by the Company Du Pont de Nemours under the trademark "Tyvek®". The surgical mesh to be sterilized is therefore humidified by exposure to water vapor, inserted into a pouch at least partly contructed of "Tyvek®" and submitted to ethylene oxide gas for sterilization. Thereafter the surgical mesh and pouch may be subjected to a drying operation to remove the humidity from the product and pouch.

For purposes of maintaining the sterility of the surgical mesh during its transportation and storage up to the moment of its use, the surgical mesh is kept inside the "Tyvek®" pouch after sterilization.

In order to maintain the surgical mesh and the pouch is a dried state, the surgical mesh and pouch may by further packaged in a moisture-impervious material, e.g. a foil pouch with or without a desiccant.

Thereafter, the sterile surgical mesh in the "Tyvek®" pouch sealed with moisture-impervious material is directly packaged in a rigid exterior container, e.g. a cardboard box or envelope to protect and maintain the shape of the surgical mesh during transport.

While the surgical mesh stored inside the pouch is indeed sterile, the outside surface of the transportation pouch is not sterile and thus it is important that the pouch does not get into a sterile area in a surgical theater.

SUMMARY OF THE INVENTION

In this technical context, it is desirable to provide a packaging that would be convenient and simple to use for the operating room staff such as non-sterile nurses and sterile nurses intended to open the packaging in view of retrieving therefrom a pouch containing the surgical mesh. In particular, it would be desirable to provide a user such as nurses with a packaging making it clear that the exterior of the pouch itself contained in the packaging is not sterile, so that the non-sterile nurse knows which packaging to open before presenting the sterile contents to the sterile nurse in the sterile surgical field.

The present invention relates to a flat package for a non sterile protective pouch receiving a sterile surgical mesh, said package having
an external envelope including a front panel and a complementary back panel,
the inner face of the front panel and the inner face of the back panel being bonded respectively with a front layer and with a back layer of an internal envelope made of a moisture-impervious material defining a storing compartment configured for receiving the said protective pouch,
the front panel and the back panel being jointed along the contours of the external envelope and, the package having an opening end comprising two tearable portions configured to separate the front panel upon which the front layer of the internal envelope is bonded from the back panel upon which the back layer of the internal envelope is attached so as to give access to the protective pouch.

The invention thus makes it possible to simultaneously open the external envelope which provides a general mechanical protection and the internal envelope made of moisture impervious material which provides a moisture protection. This single step opening sequence is a signal to a user that the pouch to which the user has access is not a sterile material and has to be treated as such. With the package of the invention, the user who opens the package does not have to open a moisture resistant barrier in addition to a general mechanical barrier, which might leave him/her in doubt as to the material the user is granted access is or not sterile. User error of inadvertently introducing non-sterile materials into the sterile operating field can result in delays in the surgical procedure, waste of contaminated surgical supplies and an increased risk of infection to the patient.

In a embodiment, the internal envelope comprises a series of welding line which joins the front layer and the back layer and defining the storing compartment, the bonding strength of the welding line being less than the bonding strength of the envelope front layer with the front panel and the envelope back layer with the back panel.

The internal envelope can be formed by a folded strip of moisture-impervious material closed by two longitudinal welding lines and a transversal welding line positioned towards the opening end.

In an embodiment, the front panel and the back panel include respectively a front grabbing tab and a back grabbing tab.

Preferably the transversal welding line is located at a distance from the front and back grabbing tab allowing grabbing the front layer with the front panel and grabbing the back layer with the back panel during opening.

In an embodiment, the transversal welding line has a V shape.

The back grabbing tab can extend along the width of back panel and/or the front grabbing tabs can be located in the middle of the front panel width.

It is envisaged that the tearable portions include a series of weakening cut made on the longitudinal edges of the external envelope.

Another aspect of the invention concerns a method of packaging a surgical mesh in a flat package comprising the steps of providing a gas permeable pouch enclosing a surgical mesh;

sterilizing the surgical mesh within the pouch by introducing a sterilizing gas in the gas permeable pouch;

introducing said pouch into a flat internal envelope including a front layer and a back layer of a moisture-impervious material;

sealing the internal envelope by a welding line;

packaging the flat internal envelope into an external envelope wherein the front layer and the back layer are bonded respectively to a front panel and a back panel of the external envelope.

In an embodiment, the method include the step of packaging the internal envelope into the external includes the step of bonding the front layer and the back layer respectively to a front panel and a back panel of the external envelope with a bonding strengh higher than bonding strength of the welding lines sealing the front layer and the back layer of the internal envelope.

BRIEF DESCRIPTION OF THE DRAWINGS

The foregoing objects and advantages of the present invention will become apparent from the reading of the following description in connection with the accompanying drawings, in which FIG. 1 includes a top view of a package according to an embodiment of the invention.

DETAILED DESCRIPTION

Reference will now be made to the drawings.

Figure 1:
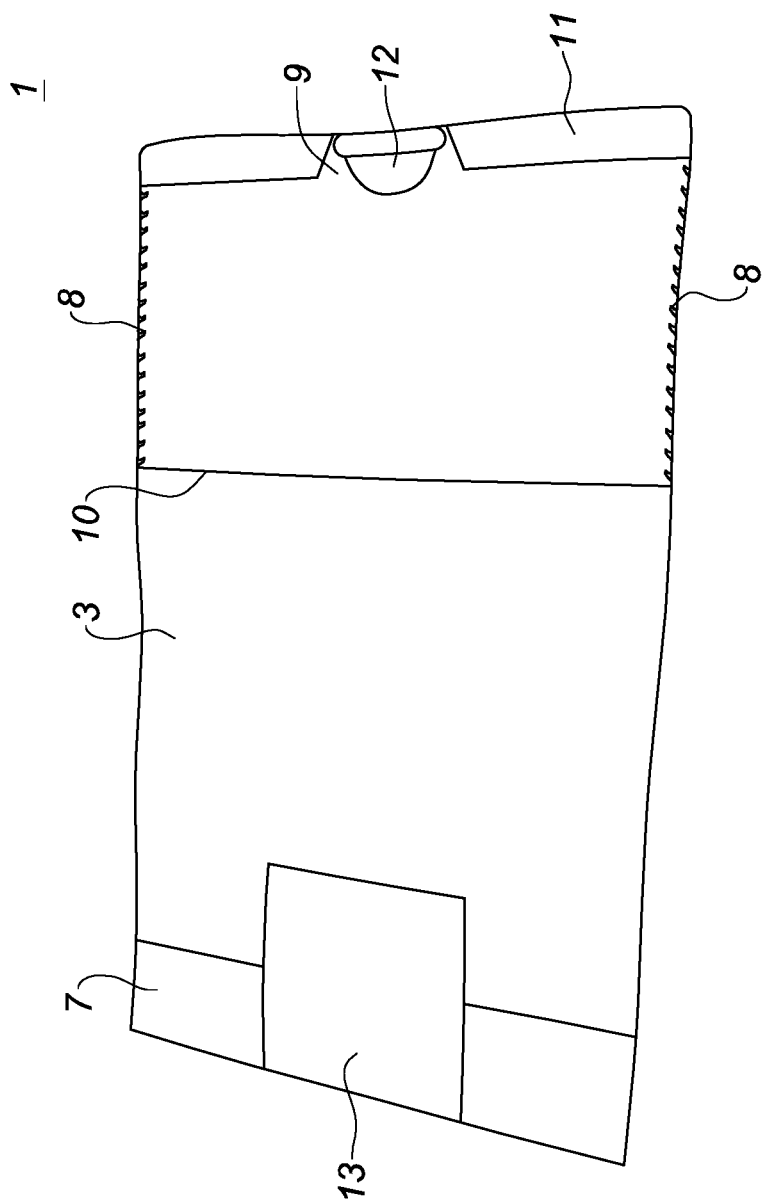
Figure 2:
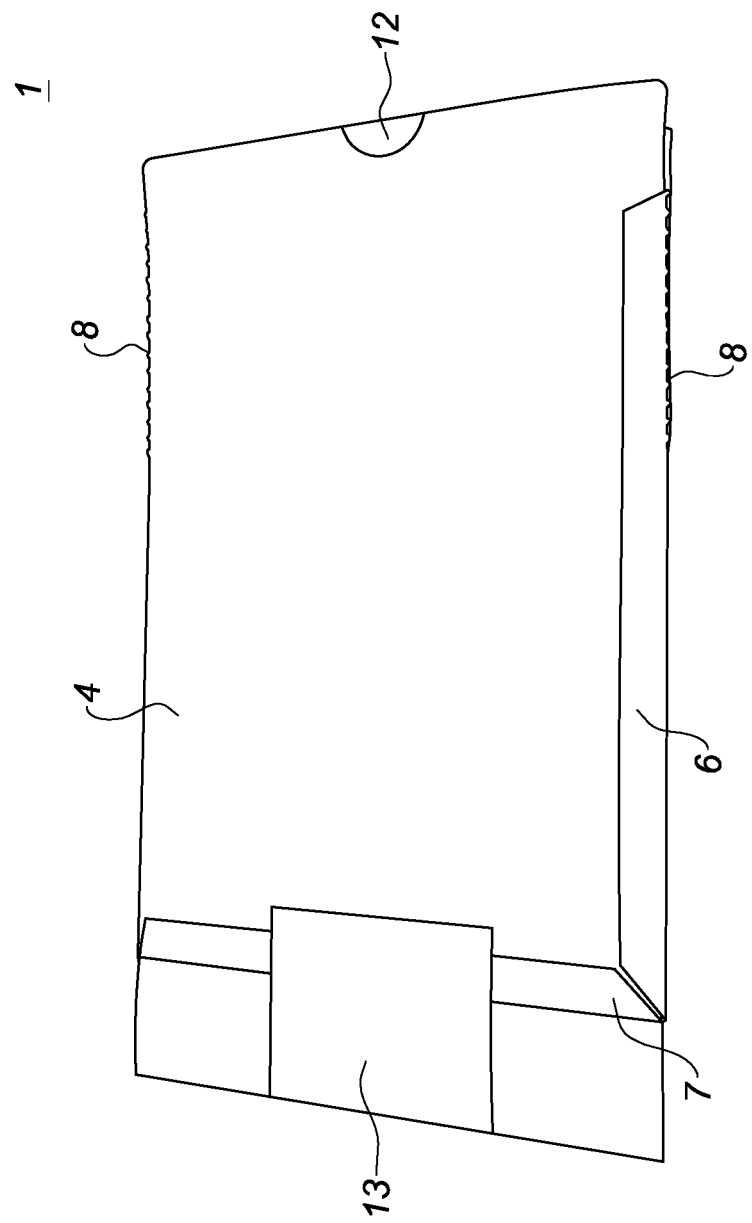
FIG. 2 includes a view from beneath of the embodiment of FIG. 1.

Turning to FIG. 1 and FIG. 2, a package 1 according to the invention is shown. The package 1 has a rectangular shape.

Package 1 includes an external envelope 2 having a front panel 3 and a back panel 4.

The external envelope 2 can be made of the single sheet which is folded and closed using a longitudinal closing flap 6 and a transversal closing flap 7.

The external envelope 2 is provided with two tearable portions 8 which define an opening A as it will be apparent later. The tearable portions 8 can be made by weakening superficial cuts carried out in the longitudinal edges of the external envelope 2.

At the opening side, the front panel 3 can be provided with a front grabbing tab 9 and a scoring line 10 and the back panel 4 can include a back grabbing tab 11. In the illustrated embodiment, the back grabbing tab 11 extends along the width of back panel 4 and the front grabbing tab 9 is located in the middle of the front panel 3 width.

The package 1 can include a tamper proof sticker 12 which is positioned on the front grabbing tab 9 and back grabbing tab 11.

At the closing side opposite the above described opening side, the package is closed by the transversal closing flap 7 which is maintained by a sticking band 13.

The external envelope 2 can be made of any suitable cardboard or laminated material.

Figure 3:
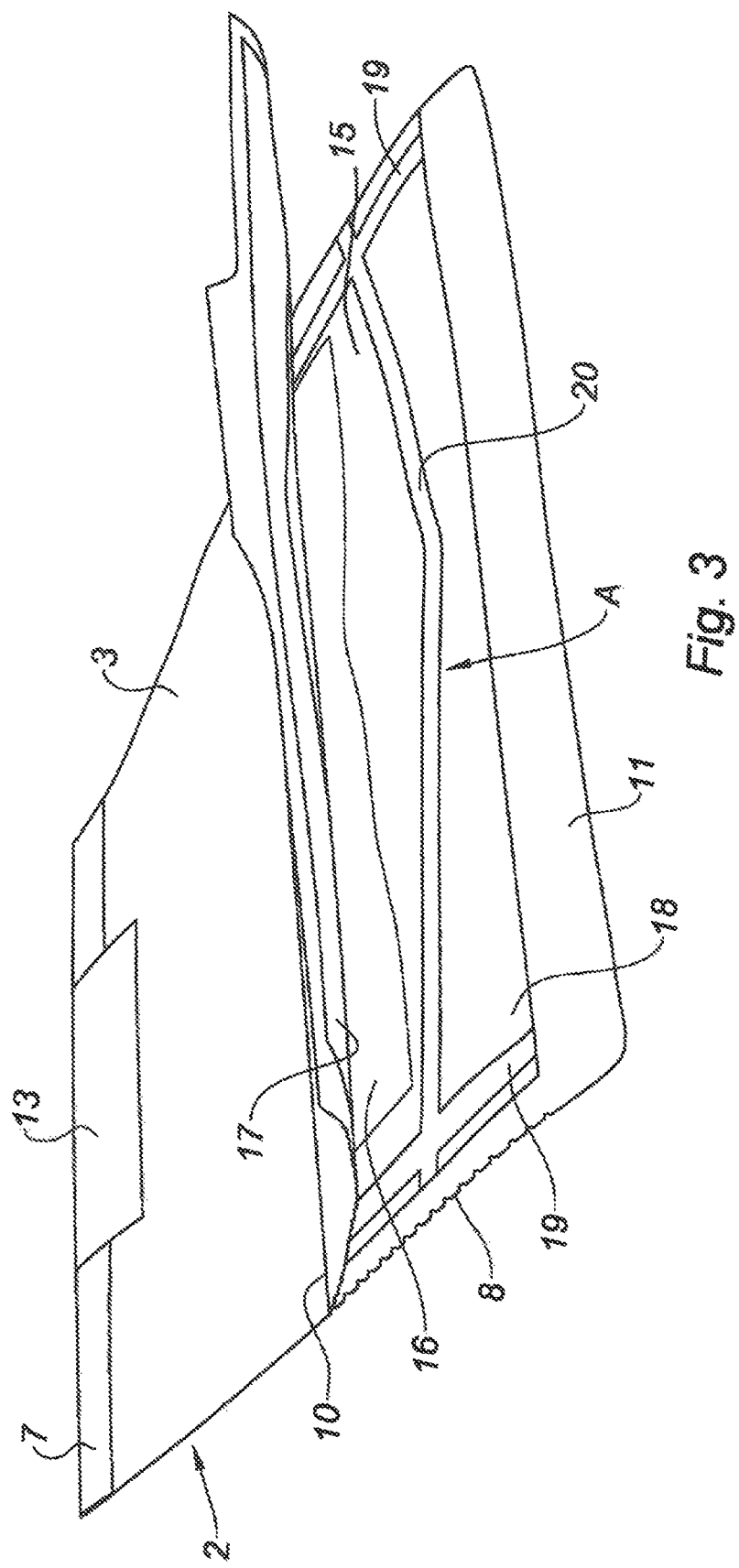
FIGS. 3 to 5 includes perspective views of the embodiment of FIG. 1 during opening.

Turning to FIG. 3, the package 1 during opening is shown.

The tamper proof sticker 12 is cut which allows a user to take hold of the front grabbing tab 9 and back grabbing tab 11.

The tearable portions 8 are torn by the user action to separate the front panel 3 from the back panel 4, thereby creating on opening A.

Figure 4:
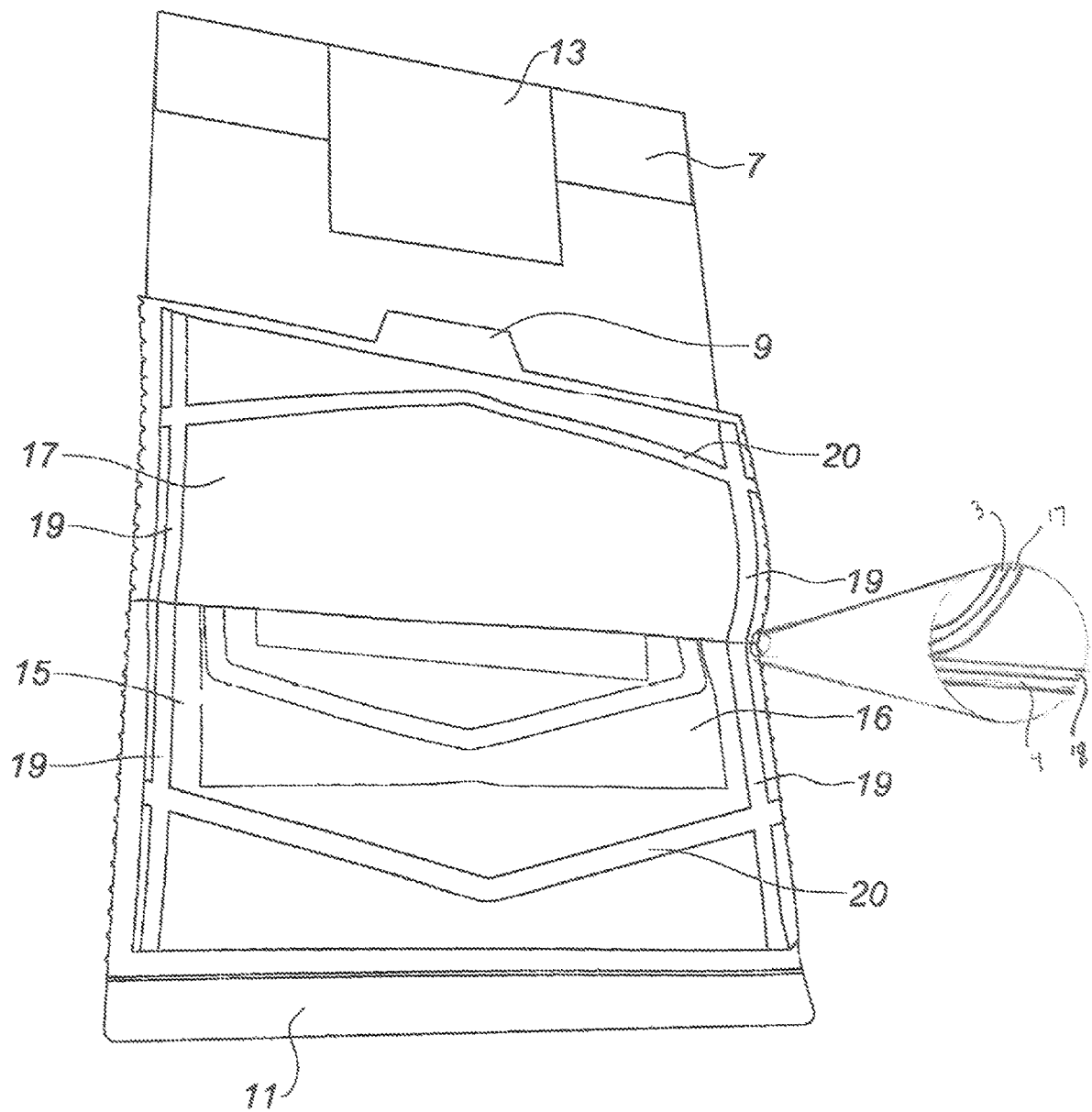
Figure 5:
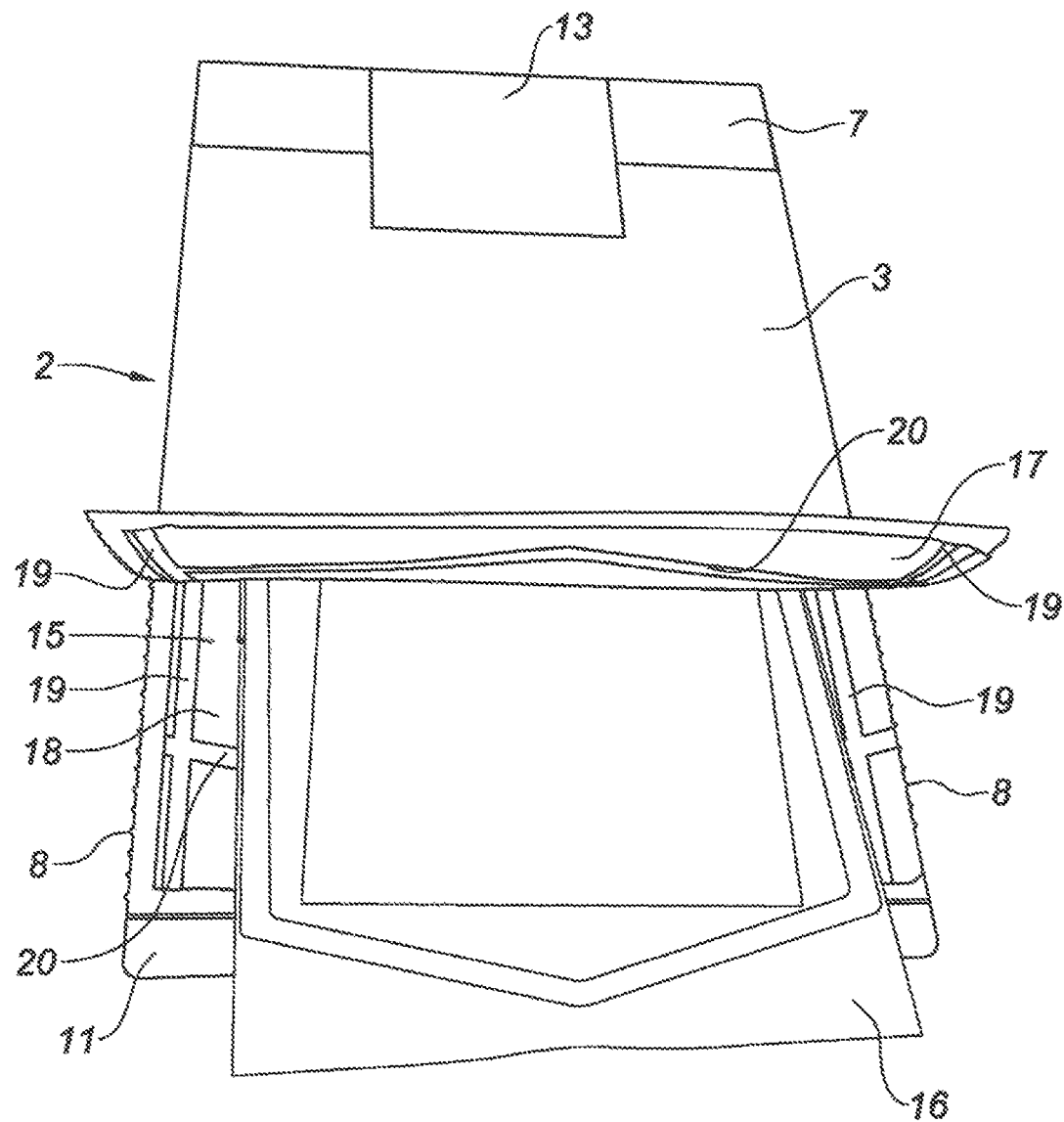

FIG. 4 shows the package having the front panel 3 folded in an open position along the scoring line 10.

Inside the external envelope 2, is an internal envelope 15 made of moisture-impervious material, such as foil, that forms a moisture barrier. The internal envelope 15 defines a flat storing compartment for a protective pouch 16 for a sterile surgical mesh.

The internal envelope 15 has a front layer 17 which is bonded onto the front panel 3 by a suitable adhesive and a back layer 18 which is bonded onto the back panel 4 by a suitable adhesive.

The internal envelope 15 is closed by a series of welding lines which joins the front layer 17 and the back layer 18.

The internal envelope 15 is closed by two longitudinal welding lines 19 and by a transversal welding line 20 positioned towards the package opening A.

As can be seen on FIG. 4, the transversal welding line 20 is located at a distance from the front and back grabbing tab 11; this allows grabbing the front layer 17 with the front panel 3 and grabbing the back layer 18 with the back panel 4 during opening.

The bonding strength of the welding lines 19,20 is less than the bonding strength of the internal envelope 15 front layer 17 with the front panel 3 and the bonding strength of the internal envelope 15 back layer 18 with the back panel 4.

Thus, when opening the package 1; a non sterile user gets hold of the front grabbing tab 9 and of the back grabbing tab 11. This ruptures the tearable portions 8 but the front layer 17 remains attached onto the front panel 3 and the back layer 18 remains attached onto the back panel 4.

When accessing the storing compartment, the non sterile user pulls with one hand, the front panel 3 and on the front layer 17 and, with the other hand, the back panel 4 and the back layer 18.

Thus, the user is given access to the storing compartment in one single operation, where a protective pouch 16 can be removed from the package. Thereafter, the non-sterile user can open the second barrier of the protective pouch 16 to present the sterile contents of the pouch, the surgical mesh, to the sterile nurse to be placed in the sterile operating field.

This proves to be important because users tend to understand that breaking two barriers are required before accessing a sterile object such as a surgical mesh.

The invention makes it possible to ensure that the opening of the moisture-impervious barrier i.e. opening of the external envelope 2 and of the internal envelope 15 is clearly different from the opening a sterile barrier i.e. opening of the protective pouch 16 -.

It can be noted that the surgical mesh can be package in according to a method having the steps:
- providing a gas permeable pouch 16 enclosing a surgical mesh;
- sterilizing the surgical mesh within the pouch 16 by introducing a sterilizing gas in the gas permeable pouch 16;
- introducing said pouch 16 into a flat internal envelope 15 including a front layer 17 and a back layer 18 of a moisture-impervious material;
- sealing the internal envelope 15 by a welding line;
- packaging the flat internal envelope 15 into an external envelope 2 wherein the front layer 17 and the back layer 18 are bonded respectively to a front panel 3 and a back panel 4 of the external envelope 2.

Preferably, the step of packaging the internal envelope 15 into the external 2 includes the step of bonding the front layer 17 and the back layer 18 respectively to a front panel 3 and a back panel 4 of the external envelope 2 with a bonding strengh higher than bonding strength of the welding lines sealing the front layer 17 and the back layer 18 of the internal envelope 15.

The invention claimed is:

1. A flat package for a non sterile protective pouch receiving a sterile surgical mesh, the package comprising an external envelope including a front panel and a complementary back panel, an inner face of the front panel and an inner face of the back panel being bonded respectively with a front layer and with a back layer of an internal envelope made of a moisture-impervious material defining a storing compartment configured for receiving the protective pouch, the front panel and the back panel being jointed along contours of the external envelope and, the package having an opening end comprising two tearable portions configured to be torn to separate the front panel upon which the front layer of the internal envelope is bonded from the back panel upon which the back layer of the internal envelope is attached to open the external envelope, wherein the external envelope includes a single sheet which is folded and closed using a longitudinal closing flap, and wherein the tearable portions include a series of weakening cut made on first and second longitudinal edges of the external envelope, the first and second longitudinal edges extending between the opening end and an opposite closing end of the package, and the series of weakening cut in the first longitudinal edge overlap a portion of the longitudinal closing flap towards the opening end.

2. The package of claim 1, wherein the internal envelope comprises a series of welding line which join the front layer and the back layer and define the storing compartment, a bonding strength of the welding lines being less than a bonding strength of the envelope front layer with the front panel and the envelope back layer with the back panel.

3. The package of claim 2, wherein the front panel and the back panel include respectively a front grabbing tab and a back grabbing tab.

4. The package of claim 3, wherein a transversal welding line positioned towards the opening end is located at a distance from the front and back grabbing tab allowing grabbing the front layer with the front panel and grabbing the back layer with the back panel during opening.

5. The package of claim 4, wherein the transversal welding line positioned towards the opening end has a V shape.

6. The package of claim 4, wherein the back panel comprises a width and the back grabbing tab extends along the width of back panel.

7. The package of claim 6, wherein the front panel comprises a width and the front grabbing tab is located in a middle of the front panel width.

8. The package of claim 1, wherein the moisture-impervious material comprises foil.

9. The package of claim 1, wherein the single sheet which is folded and closed further uses a transversal closing flap.

10. The package of claim 9, wherein the transversal closing flap is maintained by a sticking band.

11. The package of claim 10, further comprising a tamper proof sticker positioned on the front grabbing tab and the back grabbing tab.

12. The package of claim 2, wherein the front and back panels are configured to be separated from each other with the front panel bonded with the front layer and the back panel bonded with the back layer to simultaneously open the internal envelope to provide access to the storing compartment and tear the tearable portions to open the external envelope in one single step, where the protective pouch can be removed from the package.

13. The package of claim 4, wherein the transversal welding line positioned towards the opening end is located between the front grabbing tab and a scoring line positioned on the front panel.

14. The package of claim 1, wherein the front panel further comprises a scoring line located between the two tearable portions and a front and back grabbing tab located along a width of the front and back panels, respectively.

15. A flat package comprising
a sterile surgical mesh enclosed within a protective pouch, the pouch having a non sterile exterior while contained within the package, and
an external envelope including a front panel and a complementary back panel, an inner face of the front panel and an inner face of the back panel being bonded respectively with a front layer and with a back layer of an internal envelope made of a moisture-impervious material defining a storing compartment including the protective pouch, the package having an opening end comprising two tearable portions configured to be torn to separate the front panel upon which the front layer of the internal envelope is bonded from the back panel upon which the back layer of the internal envelope is attached, wherein the external envelope includes a single sheet which is folded and closed using a longitudinal closing flap, and wherein the tearable portions include a series of weakening cut made in first and second longitudinal edges of the external envelope, the first and second longitudinal edges extending between the opening end and an opposite closing end of the package, and the series of weakening cut in the first longitudinal edge overlap a portion of the longitudinal closing flap towards the opening end.

16. The package of claim 15, wherein the front panel further includes a front grabbing tab located in a middle portion of a first width of the front panel and the back panel further includes a back grabbing tab extending along an entire width of the back panel.

17. The package of claim 15, wherein the internal envelope is closed and the front layer and the back layer are sealed together by two longitudinal welding lines, and a transversal welding line positioned towards the opening end and a transversal welding line positioned opposite the opening end.

18. The package of claim 15, wherein the external envelope which is folded and closed includes both the longitudinal closing flap and a transversal closing flap.

19. The package of claim 17, wherein the front panel includes a scoring line located between the two tearable portions and between the transversal welding line positioned towards the opening end and the transversal welding line positioned opposite the opening end.

20. The package of claim 15, wherein the external envelope is made of cardboard and the internal envelope is made of foil.

21. The package of claim 15, wherein the first and second longitudinal edges each further comprise a non-tearable portion on the closing end of the package, the non-tearable portion free of the series of the weakening cut.

22. The package of claim 15, wherein the internal envelope is formed by a folded strip of the moisture-impervious material closed by two longitudinal welding lines and a transversal welding line positioned towards the opening end.

23. The package of claim 15, further comprising welding lines which join the front layer to the back layer of the internal envelope and define the storing compartment, a bonding strength of the welding lines is less than a bonding strength of the front layer with the front panel and the back layer with the back panel, wherein the front and back panels are configured to be separated from each other with the front panel bonded with the front layer and the back panel bonded with the back layer to simultaneously open the internal envelope to provide access to the storing compartment and tear the tearable portions to open the external envelope in one single step.

* * * * *